United States Patent
Chia et al.

[11] Patent Number: 5,913,856
[45] Date of Patent: *Jun. 22, 1999

[54] CATHETER SYSTEM HAVING A POROUS SHAFT AND FLUID IRRIGATION CAPABILITIES

[75] Inventors: Weng-Kwen Raymond Chia, Irvine; Hosheng Tu, Tustin, both of Calif.

[73] Assignee: Irvine Biomedical, Inc., Irvine, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 09/100,176

[22] Filed: Jun. 18, 1998

Related U.S. Application Data

[63] Continuation-in-part of application No. 08/858,736, May 19, 1997, abandoned.

[51] Int. Cl.⁶ .................................................. A61B 17/36
[52] U.S. Cl. ............................................................ 606/41
[58] Field of Search .................................... 607/119, 122, 607/104, 105; 606/41, 45, 49

[56] References Cited

U.S. PATENT DOCUMENTS

| 5,313,943 | 5/1994 | Houser et al. | 607/120 |
|---|---|---|---|
| 5,409,000 | 4/1995 | Imran | 600/374 |
| 5,643,197 | 7/1997 | Brucker et al. | 607/119 |
| 5,796,846 | 6/1998 | Edwards et al. | 606/41 |

*Primary Examiner*—William E. Kamm
*Assistant Examiner*—George R. Evanisko

[57] ABSTRACT

An improved ablation catheter having a distal tip section made of flexible porous plastic material for fluid infusion and irrigation at its electrode comprises a catheter shaft having a distal section and at least one lumen extending therebetween, wherein the catheter is inserted into the chambers of the heart to create deep and large lesions by applying radiofrequency energy along with irrigated fluid to the electrode.

9 Claims, 3 Drawing Sheets

CATHETER SYSTEM HAVING A POROUS SHAFT AND FLUID IRRIGATION CAPABILITIES

This is a continuation-in-part of application Ser. No. 08/858,736, filed May 19, 1997, now abandoned.

FIELD OF THE INVENTION

The present invention generally relates to improved constructions for a catheter system. More particularly, this invention relates to catheter and methods for ablating cardiac tissues via a steerable ablation catheter having a porous shaft at its tip section with fluid infusion and irrigation capabilities for ablating intracardiac tissues resulting in a deeper and larger lesion in the cardiac tissue of the heart.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias which are frequently caused by the presence of an "arrhythmogenic site" or "accessory atrioventricular pathway" close to the inner surface of the chambers of a heart. The heart includes a number of normal pathways which are responsible for the propagation of electrical signals from the upper to lower chambers necessary for performing normal systole and diastole function. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to control the emission of energy to ablate the tissue within the heart.

Of particular interest to the present invention are radiofrequency (RF) ablation protocols which have been proven to be highly effective in tachycardia treatment while exposing a patient to minimal side effects and risks. RF catheter ablation is generally performed after conducting an initial mapping study where the locations of the arrhythmogenic site and/or accessory pathway are determined. After a mapping study, an ablation catheter is usually introduced to the target heart chamber and is manipulated so that the ablation tip electrode lies exactly at the target tissue site. RF energy or other suitable energy is then applied through the tip electrode to the cardiac tissue in order to ablate the tissue of arrhythmogenic site or the accessory pathway. By successfully destroying that tissue, the abnormal signal patterns responsible for the tachycardia may be eliminated.

The impedance usually rises at the tissue contact site when RF energy is delivered through an electrode. To create a deeper and larger lesion, the surface of the tissue contact sites need to maintain a proper temperature by a cooled fluid irrigation or infusion to partially compensate for the temperature rise due to RF energy delivery. The following U.S. patents have disclosed use of plurality of irrigation ports in different manners to cool the tissue contact surface. In practice, the fluid coming out of the irrigation ports may not evenly cover all the surface area of the electrode or the tissue to be ablated. Those patents are U.S. Pat. No. 5,545,161 to Imran, U.S. Pat. No. 5,462,521 to Brucker et al., U.S. Pat. No. 5,437,662 to Nardella, U.S. Pat. No. 5,423,811 to Imran et al., U.S. Pat. No. 5,348,554 to Imran et al., and U.S. Pat. No. 5,334,193 to Nardella. However, none of the above discloses an irrigation system of cooled fluid through a porous means to form a uniform protective fluid layer around the electrode.

The tip section of a catheter is referred to here as the portion of that catheter shaft containing at least one electrode. In one embodiment, a catheter utilized in the endocardial RF ablation is inserted into a major vein or artery, usually in the neck or groin area. The catheter is then guided into an appropriate chamber of the heart by appropriate manipulation through the vein or artery. The tip of a catheter must be manipulatable by a physician from the proximal end of the catheter, so that the electrodes at the tip section can be positioned against the tissue site to be ablated. The catheter must have a great deal of flexibility in order to follow the pathway of major blood vessels into the heart. It must permit user manipulation of the tip even when the catheter body is in a curved and/or twisted configuration. The tip section of a conventional electrophysiology catheter that is deflectable usually contains one large electrode about 4 mm in length for ablation purpose. The lesion is generally not deep because of potential impedance rise of tissue in contact with the catheter electrode and the ablation time needs to be cut short. Even in the case of a conventional catheter with irrigation capabilities by utilizing a plurality of irrigation ports, the cooled fluid do not evenly and uniformly rinse the ablation electrodes.

After the exact location of a target tissue is identified, the ablation catheter may still not easily approach the target site even with assistance of an internal viewing means. This viewing situation may turn into a nightmare when an internal viewing approach becomes prohibitive or unavailable during procedures. An external ultrasonic imaging capability therefore becomes in need so that ablation is not taking place in an inappropriate location. The fluoroscope time can be substantially cut short when an external ultrasonic imaging is used instead. In the U.S. Pat. No. 4,794,931, there has been disclosed a catheter and system which can be utilized for ultrasonic imaging. However, there is no disclosure to how such a catheter and system can be utilized in conjunction with an endocardial or epicardial ablation catheter having a porous shaft with irrigation capabilities to achieve the desired ultrasonic imaging and ultimately the desired ablation.

While a radiofrequency electrophysiology ablation procedure using an existing catheter has had promising results, the tip section of a known catheter usually have only a plurality of fluid infusion ports which may not evenly rinse the electrode when contacting the tissue for ablation purpose. Therefore there is a need for a new and improved catheter for making a deeper and larger lesion in the cardiac tissue.

SUMMARY OF THE INVENTION

In general, it is an object of the present invention to provide an improved catheter for even fluid infusion and irrigation. This capability of even fluid infusion may be applicable to the drug delivery means to a tumor or cancer site. The capability of even fluid irrigation may be applicable to means of cooling off the tissue contact site due to impedance rise of the ablation electrodes. An ablation catheter with porous tip section having at least one electrode can be used in effectively ablating the arrhythmogenic point or region of a patient. This catheter is particularly useful for treating the patient with atrial fibrillation (AFib) indications as a result of its cooled electrodes. In one embodiment, an ablation catheter system comprises a catheter shaft having a distal end, a proximal end and at least one lumen extending therebetween. A handle is attached to the proximal end of said catheter shaft. A distal tip section of the catheter shaft which is proximal to the distal end, comprises a porous shaft having fluid infusion and irrigation capabilities, wherein the pore sizes of the porous shaft range from 5 to 1000 microns. This porous substrate with a pore size range of 5 to 1000 microns is also typically known as the microporous substrate. It is another object to provide a catheter with a shaft made of flexible porous plastic material.

A fluid source is positioned at one end of the catheter for supplying a fluid flow through the lumen of said catheter shaft to the tip section which is constructed of a porous substrate, such as a flexible porous plastic material. Therefore at ablation time, the tip section with at least one electrode is positioned against the tissues to be ablated. The fluid is continuously or intermittently supplied through the porous shaft to evenly cover and rinse the electrode so that the impedance rise at the contact site is substantially reduced. In still another embodiment, a porous metal electrode is employed so that the fluid will flow out of the porous electrode while delivering RF energy. The porosity of said porous metal electrode is appropriate for fluid irrigation of a fluid flow rate preferably in the range of 5 cc/min to 20 cc/min. By cooling off the electrode during RF energy delivery will result in optimal ablation efficiency and a desired deep and large lesion.

The ablation catheter further comprises a steering mechanism at the handle for controlling the deflection of said distal tip section having a porous shaft with fluid infusion and irrigation capabilities. Usually a rotating ring or a push-pull plunger is employed in the steering mechanism. In another embodiment, the steerable ablation catheter comprises a bi-directional deflection or multiple curves deflection of the tip section having a porous shaft. One end of the steering wire is attached at certain point of the tip section of said catheter shaft. The other end is attached to the steering mechanism at the handle. The steering mechanism on a steerable catheter or device is well-known to those who are skilled in the art.

A fluid conveying lumen is associated with the elongate catheter shaft, and is preferably disposed within the catheter shaft along the longitudinal axis thereof. The lumen is adapted to communicate with a fluid supply source to convey fluid from the source and through the lumen to be discharged through the porous shaft of the porous tip section and diffuse out of the tip section containing at least one electrode.

The invention also comprises a method and system for controlling the flow rate of fluid through the lumen to optimize the cooling effect of the energy delivering electrode of the catheter. The control system preferably regulates the flow rate based on signals representative of the temperature of the catheter tip and/or tissue impedance.

At least one conducting wire which is soldered to the electrode passes through the lumen of the inner catheter and the interior void of the handle and is thereafter soldered to a contact pin of the connector secured at the proximal end of the handle. Therefrom, the conducting wire is connected to an external RF generator for ablation operations and/or to an EKG monitor for recording and display of the endocardial or epicardial electrical signal.

In an additional embodiment, the ablation system further comprises a temperature sensing and close-loop temperature control mechanism for the electrode having at least one temperature sensor at the tissue contact site of the electrodes. The location of the temperature sensor is preferably in the very proximity of one of the electrodes. In a still further embodiment, a method for operating an ablation catheter further comprises a programmed temperature control mechanism for independently controlling the delivery of RF energy of each electrode of the ablation catheter.

In a particular embodiment, the length of at least one electrode is 4 mm or longer. The material for the electrodes may consist of conductive metals such as platinum, iridium, gold, silver, stainless steel, Nitinol, or an alloy of their mixture. In a still further embodiment, the tip section of the catheter shaft comprises at least one electrode which is formed of a porous conducting material. The porous conducting metal and its fabrication to form an electrode is well known to those who are skilled in the art. In another embodiment, the electrodes to be placed outside of and wrapped around the porous tip section of the catheter shaft of this invention are formed of a flexible metal mesh or coil.

A method for operating a steerable ablation catheter system having at least one electrode at the tip section having a porous shaft, within a heart chamber comprises: percutaneously introducing the catheter system through a blood vessel to the heart chamber; deflecting the distal section of the catheter about a transverse axis to position the tip section with at least one electrode near a target region on an interior wall of the heart chamber; intimately contacting the electrode with the intracardiac tissue; applying radiofrequency energy to the target location through the electrode; and cooling the electrodes by releasing cooled fluid through the porous shaft at said distal tip section.

Another object of the invention is to provide a catheter and methods in which it is possible to view the area to be ablated prior to ablation to ensure that ablation is being carried out in an appropriate location. The tip section having a porous shaft is encoded with plurality of markers which are visible to ultrasonic energy. The markers have been provided in the form of encapsulated air bubbles.

The catheter system of the present invention have several significant advantages over known catheter or ablation techniques. In particular, the evenly cooled electrode of a steerable ablation catheter of this invention may result in a deeper and larger lesion which is highly desirable in the AFib treatment.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
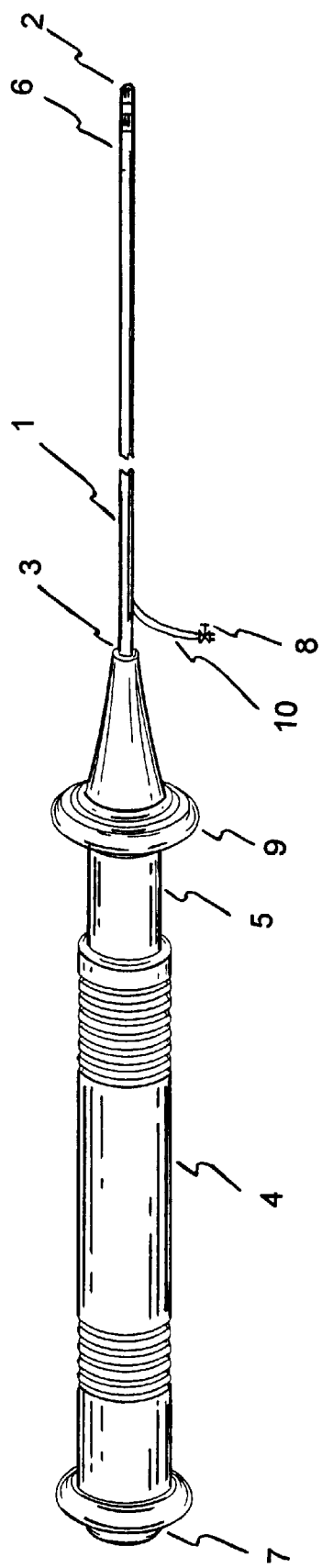
FIG. 1 is an overall view of a catheter having a porous shaft at its distal tip section constructed in accordance with the principles of the present invention.

FIG. 1 shows a perspective view of the catheter having fluid infusion and irrigation means. An ablation catheter constructed in accordance with the principles of the present invention comprises: a catheter shaft 1 having a distal tip section 6, distal end 2, a proximal end 3, and at least one lumen extending therebetween. The catheter comprises a fluid infusion mechanism 10 close to the proximal end 3 of the catheter shaft 1. A control valve 8 is secured to the fluid infusion means for providing fluid to the distal tip section 10 which is externally connected to a fluid supply source having a pump (not shown). A handle 4 is attached to the proximal end 3 of said catheter shaft 1.

The connector 7 secured at the proximal end of the catheter system, is part of the handle section 4. The handle has one steering mechanism 5. The steering mechanism 5 is to deflect the tip section 6 of the catheter shaft 1 for catheter maneuvering and positioning. By pushing the front plunger 9 of the handle 4, the tip section of the catheter tip section deflects to one direction. By pulling the front plunger 9, the tip section returns to its neutral position. In another embodiment, the steering mechanism 5 at the handle 4 comprises means for providing a plurality of deflectable curves on the distal tip section 6 of the catheter.

Figure 2:
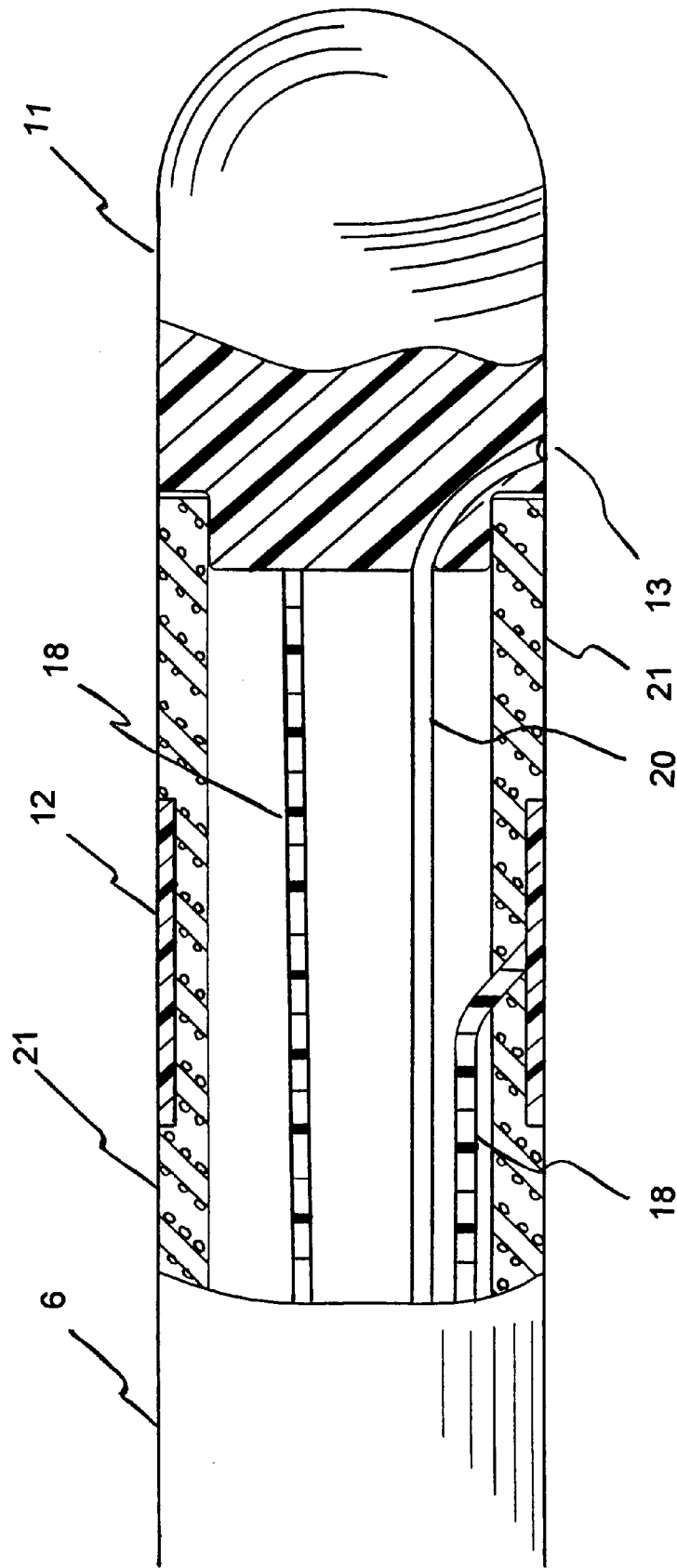
FIG. 2 is a close-up view of the distal section of the catheter comprising a porous shaft with fluid infusion and irrigation capabilities.

FIG. 2 shows a close-up view of the distal section of the catheter with a porous shaft, wherein the pore sizes of the porous shaft range from 5 to 1000 microns. This substrate with a pore size range of 5 to 1000 microns is also typically known as the microporous substrate. In one embodiment, the catheter shaft 21 of the tip section 6 is constructed of a flexible porous plastic material. Since the catheter shaft is made of plastic material, it is flexible and deflectable to be used as a medical device. FIG. 2 shows that the entire distal tip section comprises a flexible porous plastic material, wherein said flexible porous plastic material surrounds the at least one electrode on all sides and underneath except an outer surface. The porosity of said plastic material is such that the fluid flow rate from the fluid infusion mechanism 6 may be between approximately 5 ml/min to 20 ml/min. The tip section 6 of the catheter shaft 1 comprises a tip electrode 11 and at least one band electrode 12. The electrodes are formed of a conducting material. In one other embodiment, at least one electrode is a metal mesh or a metal coil securely wrapped outside of the catheter shaft 6 of the catheter system.

Figure 3:
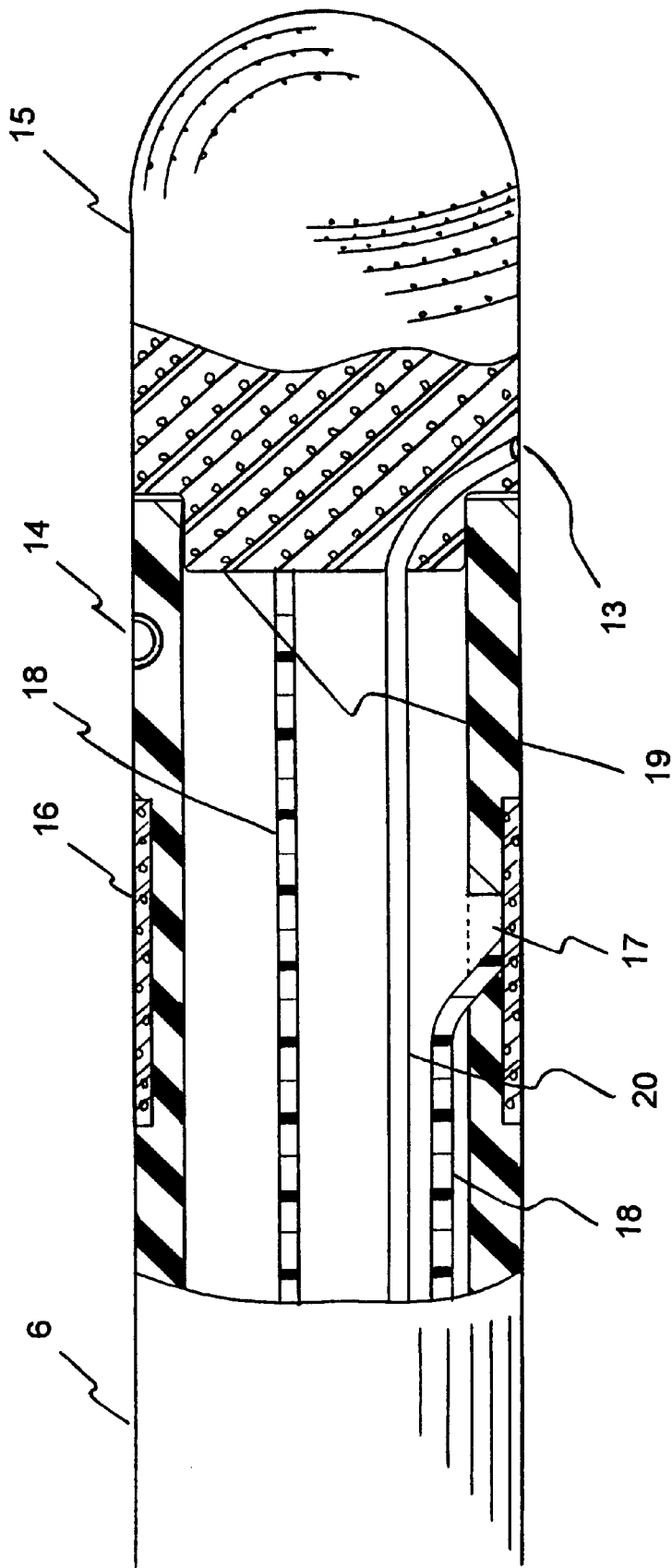
FIG. 3 is a close-up view of the distal section of the catheter comprising porous metal electrode means.

FIG. 3 shows a cross-sectional view of the tip section having at least one porous electrode with at least one temperature sensor 13 and ultrasonic imaging capabilities. The tip electrode 15 and at least one band electrode 16 are constructed of conductive porous metal. To convey the fluid through the porous electrodes to the exterior of the catheter, a connecting passage 17 is provided for the fluid to flow into and through the band electrode 16. The fluid will flow into the tip electrode 15 through the permeable surface 19 of said tip electrode 15.

In order to enhance the ablation positioning of said ablation catheter, the electrode is encoded with at least one marker 14 which is visible to ultrasonic energy. Such markers 14 are provided in the form of encapsulated air bubbles. Several markers 14 are placed in the proximity of the electrodes 15 or 16 in a way so that the exact location of the tip section 6 is visible to an external ultrasonic energy. By way of example, the bubble in a marker can be formed by introducing air by a syringe (not shown) penetrating the wall of the substrate of said catheter shaft and thereafter is sealed by epoxy.

The electrode has an insulated conducting wire 18 secured to the electrode, which passes through the lumen of the catheter shaft 1 and is soldered to a contact pin of the connector 7 at the proximal end of the handle 4. The conducting wire from the connector end is externally connected to an EKG for diagnosis or to an RF generator during an electrophysiology ablation procedure. Therefrom, the RF current is transmitted through the conducting wire to the electrode and delivered the energy to the target tissue.

A temperature sensor 13, either a thermocouple means or a thermister means, is constructed at the proximity of the electrodes 11, 12, 15 or 16 to measure the tissue contact closed-loop temperature when RF energy is delivered. The temperature sensing wire 20 from the thermocouple or thermister is connected to one of the contact pins (not shown) of the connector 7 and externally connected to a transducer and to a temperature controller. The temperature reading is thereafter relayed to a close-loop control mechanism to adjust the RF current output. The RF current delivered is thus controlled by the temperature sensor reading or by a pre-programmed control algorithm.

The catheter of this invention is to provide fluid communication and commensurate flow of fluid originating inside the tip section of the catheter shaft to the electrode exterior surface through a porous shaft, either a flexible porous plastic shaft at its distal tip section or a porous metal electrode, which directs the fluid flow from inside the catheter shaft over the exterior surface of the electrode to provide a fluid protective layer surrounding the electrode to minimize temperature elevation of the electrode with biological tissues.

EXAMPLE NO. 1

A microporous substrate of high density polyethylene (HDPE) tubular bar is used in the following experiment. The microporous HDPE is supplied by GenPore (P.O. Box 380, Reading, Pa. 19607) as a tubular form with an outside diameter of 2 mm and a wall thickness of 0.3 mm. It equivalent pore size is rated as 500 microns. Water at room temperature and at a differential pressure of 1 psi is used to study the liquid permeate rate through said microporous plastic material.

A wide range of materials for controlled porosity applications includes the following materials: ultrahigh molecular weight polyethylene, high density polyethylene, low density polyethylene, very low density polyethylene, polypropylene, ethylene vinyl acetate, polystyrene, epoxy glass or phenol glass, etc. The shapes available include tubular bar, sheet, slab, and rod. The controlled pore sizes of a microporous plastic material from 5 to 1000 microns are available, depending on the requirements of high volume flow of the liquid or high filtration efficiency. The microporous substrate polymers have the characteristics of high-strength, lightweight, high purity and sterilizability to be used as a medical device.

The liquid permeate rate is expressed as $Q = k \times \Delta P \times A$

Where Q is the liquid permeate rate, $cc/(min\text{-}psi\text{-}mm^2)$ k is a constant as a function of porosity, wall thickness, liquid type, and material specificity $\Delta P$ is the applied differential pressure, psi A is the effective permeating area perpendicular to the liquid flow The constant "k" is determined as $0.4\ cc/(min\text{-}psi\text{-}mm^2)$ for the HDPE tested. This translates to a liquid permeate rate of 5 cc/min for a microporous substrate having an effective permeating area of 12 $mm^2$ and an applied differential pressure of 1 psi.

From the foregoing, it should now be appreciated that an improved ablation catheter having a porous shaft and an fluid infusion capability has been disclosed for ablation procedures, including endocardial, epicardial, or body tissue and drug delivery to a tumor or cancer site. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter comprising:
   a catheter shaft having a distal tip shaft section, a distal end, a proximal end, and at least one lumen extending between the distal end and the proximal end, wherein the distal tip section is flexible;
   at least one electrode disposed at the distal tip section;
   fluid irrigation means for providing fluid to the distal tip section, wherein the fluid irrigation means is externally connected to a fluid supply source;
   a handle attached to the proximal end of the catheter shaft; wherein
   the entire distal tip section comprises a flexible porous plastic material, wherein said flexible porous plastic material surrounds the at least one electrode on all sides and underneath the at least one electrode except for an outer surface of the at least one electrode, wherein the porous plastic material is adapted for fluid infusion, effusion and irrigation of the distal tip section of the catheter shaft, wherein fluid is effused out of pores of the porous plastic material, and wherein fluid irrigates and cools the at least one electrode by evenly covering and rinsing the at least one electrode so that an impedance rise at the contact site between the at least one electrode and tissue is substantially reduced.

2. The catheter of claim 1, wherein the pore size of the porous plastic materials is in the range of 5 to 1000 microns.

3. The catheter as in claim 1 further comprising a steering mechanism at the handle for controlling deflection of the distal tip section of the catheter shaft.

4. The catheter of claim 3, wherein the steering mechanism provides a plurality of deflectable curves on the distal tip section of the catheter shaft.

5. The catheter of claim 1, wherein the at least one electrode is comprised of a metal mesh.

6. The catheter as in claim 1 further comprising a temperature sensor mounted at the proximity of the at least one electrode and the catheter system being equipped with a closed-loop temperature controller, wherein the temperature sensor is adapted for providing temperature signals to the closed-loop temperature controller for controlling a RF current delivery.

7. The catheter as in claim 1 further comprising at least one ultrasonic visible marker being disposed in the proximity of the at least one electrode at the distal tip section.

8. An ablation catheter system comprising:
   a catheter shaft having a distal tip shaft section, a distal end, a proximal end, and at least one lumen extending between the distal end and the proximal end, wherein the distal tip section is flexible;
   at least one electrode disposed at the distal tip section;
   a handle attached to the proximal end of the catheter shaft;
   fluid irrigation means for providing fluid to the distal tip section, wherein the fluid irrigation means is externally connected to a fluid supply source;
   wherein the entire distal tip section comprising a flexible porous plastic material, wherein said flexible porous plastic material surrounds the at least one electrode on all sides and underneath the at least one electrode except for an outer surface of the at least one electrode, wherein the porous plastic material is adapted for fluid infusion, effusion and irrigation of the distal tip section of the catheter shaft, wherein fluid is effused out of pores of the porous plastic material, and wherein fluid irrigates and cools the at least one electrode by evenly covering and rinsing the at least one electrode so that an impedance rise at the contact site between the at least one electrode and tissue is substantially reduced; and
   a RF current generating means for generating a RF current, wherein the RF current is delivered to the at least one electrode.

9. The ablation catheter system of claim 8, wherein the at least one electrode is made of a material selected from the group consisting of platinum, iridium, gold, silver, stainless steel, and Nitinol.

* * * * *